(12) United States Patent
Birchall, Jr. et al.

(10) Patent No.: US 10,918,494 B2
(45) Date of Patent: Feb. 16, 2021

(54) ORTHOPEDIC IMPLANT WITH INTEGRATED CORE

(71) Applicant: K2M, Inc., Leesburg, VA (US)

(72) Inventors: Charles F. Birchall, Jr., Mentor, OH (US); Lee A. Strnad, Richfield, OH (US)

(73) Assignee: K2M, Inc., Leesburg, VA (US)

( * ) Notice: Subject to any disclaimer, the term of this patent is extended or adjusted under 35 U.S.C. 154(b) by 98 days.

(21) Appl. No.: 16/096,113

(22) PCT Filed: Apr. 25, 2017

(86) PCT No.: PCT/US2017/029316
§ 371 (c)(1),
(2) Date: Oct. 24, 2018

(87) PCT Pub. No.: WO2017/189517
PCT Pub. Date: Nov. 2, 2017

(65) Prior Publication Data
US 2019/0142605 A1    May 16, 2019

Related U.S. Application Data

(60) Provisional application No. 62/327,887, filed on Apr. 26, 2016.

(51) Int. Cl.
*A61F 2/44* (2006.01)
*A61F 2/30* (2006.01)

(52) U.S. Cl.
CPC ........ *A61F 2/4425* (2013.01); *A61F 2/30744* (2013.01); *A61F 2/442* (2013.01); *A61F 2/4465* (2013.01); *A61F 2002/302* (2013.01); *A61F 2002/30014* (2013.01); *A61F 2002/30069* (2013.01); *A61F 2002/3082* (2013.01);
(Continued)

(58) Field of Classification Search
CPC ... A61F 2/442; A61F 2/4425; A61F 2002/443
See application file for complete search history.

(56) References Cited

U.S. PATENT DOCUMENTS

| | | |
|---|---|---|
| 3,867,728 A | 2/1975 | Stubstad et al. |
| 4,309,777 A | 1/1982 | Patil |

(Continued)

FOREIGN PATENT DOCUMENTS

WO    2010034287 A2    4/2010

OTHER PUBLICATIONS

Extended European Search Report including Written Opinion for Application No. EP17790236.8 dated Oct. 31, 2019.
(Continued)

*Primary Examiner* — Julianna N Harvey
(74) *Attorney, Agent, or Firm* — Lerner, David, Littenberg, Krumholz & Mentlik, LLP

(57) ABSTRACT

Orthopedic implants constructs include one or two rigid monolithic plates and a core that is integrally formed within an interior space within a rigid monolithic plate. An exemplary construct that includes two plates between which is a core that is interengaged with each plate, the two plates thereby forming a generally disc-like shaped construct with opposing tissue contacting surfaces. The constructs are suitable, for example for spinal interbody fusion and artificial disc applications.

20 Claims, 4 Drawing Sheets

(52) U.S. Cl.
CPC ............. *A61F 2002/3084* (2013.01); *A61F 2002/3093* (2013.01); *A61F 2002/30113* (2013.01); *A61F 2002/30115* (2013.01); *A61F 2002/30387* (2013.01); *A61F 2002/30563* (2013.01); *A61F 2002/30593* (2013.01); *A61F 2002/30604* (2013.01); *A61F 2002/30622* (2013.01); *A61F 2002/30836* (2013.01); *A61F 2002/30838* (2013.01); *A61F 2002/30884* (2013.01); *A61F 2002/30892* (2013.01); *A61F 2002/30904* (2013.01); *A61F 2002/443* (2013.01); *A61F 2310/00023* (2013.01)

(56) References Cited

U.S. PATENT DOCUMENTS

| | | | |
|---|---|---|---|
| 4,911,718 | A | 3/1990 | Lee et al. |
| 4,932,969 | A | 6/1990 | Frey et al. |
| 4,932,975 | A | 6/1990 | Main et al. |
| 4,946,378 | A | 8/1990 | Hirayama et al. |
| 4,997,432 | A | 3/1991 | Keller |
| 5,002,576 | A | 3/1991 | Fuhrmann et al. |
| 5,062,850 | A | 11/1991 | MacMillan et al. |
| 5,071,437 | A | 12/1991 | Steffee |
| 5,171,281 | A | 12/1992 | Parsons et al. |
| 5,314,477 | A | 5/1994 | Marnay |
| 5,314,478 | A | 5/1994 | Oka et al. |
| 5,370,697 | A | 12/1994 | Baumgartner |
| 5,401,269 | A | 3/1995 | Buttner-Janz et al. |
| 5,458,642 | A | 10/1995 | Beer et al. |
| 5,458,643 | A | 10/1995 | Oka et al. |
| 5,534,029 | A | 7/1996 | Shima |
| 5,534,030 | A | 7/1996 | Navarro et al. |
| 5,545,229 | A | 8/1996 | Parsons et al. |
| 5,556,431 | A | 9/1996 | Buttner-Janz |
| 5,562,738 | A | 10/1996 | Boyd et al. |
| 5,674,294 | A | 10/1997 | Bainville et al. |
| 5,824,094 | A | 10/1998 | Serhan et al. |
| 5,893,889 | A | 4/1999 | Harrington |
| 6,139,579 | A | 10/2000 | Steffee et al. |
| 6,162,252 | A | 12/2000 | Kuras et al. |
| 6,348,071 | B1 | 2/2002 | Steffee et al. |
| 6,368,350 | B1 | 4/2002 | Erickson et al. |
| 6,369,350 | B1 | 4/2002 | Norris |
| 6,395,032 | B1 | 5/2002 | Gauchet |
| 6,402,785 | B1 | 6/2002 | Zdeblick et al. |
| 6,419,706 | B1 | 7/2002 | Graf |
| 6,527,804 | B1 | 3/2003 | Gauchet et al. |
| 6,533,818 | B1 | 3/2003 | Weber et al. |
| 6,562,624 | B2 | 5/2003 | Adachi et al. |
| 6,579,320 | B1 | 6/2003 | Gauchet et al. |
| 6,582,468 | B1 | 6/2003 | Gauchet et al. |
| 6,592,624 | B1 | 7/2003 | Fraser et al. |
| 6,607,558 | B2 | 8/2003 | Kuras |
| 6,626,943 | B2 | 9/2003 | Eberlein et al. |
| 6,645,248 | B2 | 11/2003 | Casutt |
| 6,669,732 | B2 | 12/2003 | Serhan et al. |
| 6,682,562 | B2 | 1/2004 | Viart et al. |
| 6,726,720 | B2 | 4/2004 | Ross et al. |
| 6,733,532 | B1 | 5/2004 | Gauchet et al. |
| 6,735,532 | B2 | 5/2004 | Freed et al. |
| 6,749,635 | B1 | 6/2004 | Bryan |
| 6,793,678 | B2 | 9/2004 | Hawkins |
| 6,893,465 | B2 | 5/2005 | Huang |
| 7,128,761 | B2 | 10/2006 | Kuras et al. |
| 7,153,325 | B2 | 12/2006 | Kim et al. |
| 7,156,848 | B2 | 1/2007 | Ferree |
| 7,169,181 | B2 | 1/2007 | Kuras |
| 7,250,060 | B2 | 7/2007 | Trieu |
| 7,442,211 | B2 | 10/2008 | de Villiers et al. |
| 7,585,325 | B2 | 9/2009 | Schneid et al. |
| 7,731,753 | B2 | 6/2010 | Reo et al. |
| 7,850,697 | B2 | 12/2010 | Ross et al. |
| 7,887,592 | B2 * | 2/2011 | Koske .............. A61F 2/442 623/17.11 |
| 7,905,921 | B2 | 3/2011 | Kim et al. |
| 8,038,715 | B2 | 10/2011 | Kim et al. |
| 8,182,534 | B2 | 5/2012 | Ogilvie et al. |
| 8,277,508 | B2 | 10/2012 | Trieu |
| 8,377,138 | B2 | 2/2013 | Reo et al. |
| 8,388,685 | B2 | 3/2013 | Lombardo et al. |
| 8,403,987 | B2 | 3/2013 | Reo et al. |
| 8,506,631 | B2 | 8/2013 | de Villiers et al. |
| 8,518,116 | B2 | 8/2013 | Lombardo et al. |
| 8,734,518 | B2 | 5/2014 | Lombardo et al. |
| 8,808,381 | B2 | 8/2014 | Kim et al. |
| 8,998,989 | B2 | 4/2015 | Kim et al. |
| 9,044,278 | B2 | 6/2015 | Tanaka |
| 9,084,688 | B2 | 7/2015 | Hes et al. |
| 9,089,439 | B2 | 7/2015 | Baumgartner et al. |
| 9,278,007 | B2 | 3/2016 | Robinson |
| 2001/0016773 | A1 | 8/2001 | Serhan et al. |
| 2001/0032017 | A1 | 10/2001 | Alfaro et al. |
| 2002/0022888 | A1 | 2/2002 | Serhan et al. |
| 2003/0045939 | A1 | 3/2003 | Casutt |
| 2003/0074066 | A1 | 4/2003 | Errico et al. |
| 2003/0100951 | A1 | 5/2003 | Serhan et al. |
| 2003/0135277 | A1 | 7/2003 | Bryan et al. |
| 2003/0187506 | A1 | 10/2003 | Ross et al. |
| 2003/0208271 | A1 | 11/2003 | Kuras |
| 2004/0054411 | A1 | 3/2004 | Kelly et al. |
| 2004/0068320 | A1 | 4/2004 | Robie et al. |
| 2004/0122517 | A1 | 6/2004 | Kuras |
| 2004/0143332 | A1 | 7/2004 | Krueger et al. |
| 2004/0193273 | A1 | 9/2004 | Huang |
| 2004/0249462 | A1 | 12/2004 | Huang |
| 2004/0267367 | A1 | 12/2004 | O'Neil |
| 2005/0027300 | A1 | 2/2005 | Hawkins et al. |
| 2005/0131544 | A1 | 6/2005 | Kuras et al. |
| 2005/0192671 | A1 | 9/2005 | Bao et al. |
| 2005/0197702 | A1 | 9/2005 | Coppes et al. |
| 2005/0216081 | A1 | 9/2005 | Taylor |
| 2005/0261772 | A1 | 11/2005 | Filippi et al. |
| 2005/0288788 | A1 | 12/2005 | Dougherty-Shah |
| 2006/0025862 | A1 | 2/2006 | Villiers et al. |
| 2006/0229724 | A1 | 10/2006 | Lechmann et al. |
| 2006/0241760 | A1 | 10/2006 | Randall et al. |
| 2006/0265075 | A1 | 11/2006 | Baumgartner et al. |
| 2006/0276900 | A1 | 12/2006 | Carpenter |
| 2007/0055378 | A1 | 3/2007 | Ankney et al. |
| 2007/0270958 | A1 | 11/2007 | Albans et al. |
| 2008/0288073 | A1 * | 11/2008 | Renganath .............. A61F 2/4425 623/17.12 |
| 2009/0088853 | A1 | 4/2009 | Ogilvie et al. |
| 2009/0118836 | A1 | 5/2009 | Cordaro |
| 2009/0326658 | A1 | 12/2009 | Allard |
| 2010/0070036 | A1 | 3/2010 | Implicito |
| 2010/0274358 | A1 | 10/2010 | Mueller et al. |
| 2011/0319996 | A1 | 12/2011 | Barrall |
| 2012/0191189 | A1 * | 7/2012 | Huang .............. A61F 2/4425 623/17.11 |
| 2012/0215314 | A1 | 8/2012 | Bennett et al. |
| 2014/0277482 | A1 * | 9/2014 | Gfeller .............. B29C 45/14467 623/17.16 |
| 2014/0316524 | A1 | 10/2014 | Zimmers et al. |
| 2015/0039089 | A1 | 2/2015 | Balasubramanian et al. |

OTHER PUBLICATIONS

Extended European Search Report for European Application No. 16195736 dated Mar. 17, 2017, 10 pages.

Spinel Kinetics, "Quality of Life, Quality of Motion", M6L Artificial Lumbar Disc product brochure, 2013, 6 pages.

International Search Repot dated Aug. 24, 2017 issued in corresponding PCT Appln. No. PCT/US17/029316.

* cited by examiner

ORTHOPEDIC IMPLANT WITH INTEGRATED CORE

RELATED APPLICATIONS

This application claims the benefit under 35 U.S.C. § 119(e) to U.S. Provisional Application Ser. No. 62/322,435 filed Apr. 26, 2016, the entirety of which is incorporated herein by reference.

FIELD

The present application describes various exemplary implants for orthopedic prostheses, particularly the spine.

DESCRIPTION OF THE RELATED ART

Orthopedic implants for joint interfaces may address correction with one of fixed/fused constructs and dynamic constructs. In the spine, such devices include interbody implants for fixation and fusion, and disc replacements that provide stability and are designed to preserve and confer motion between vertebral bodies. Existing interbody device implants, both fusion cages and total discs, provide options for correction but often fall short of delivering long term benefits to patients due to insufficient or loss over time of correction (loss of angle of the device), subsidence or compression failure of device (loss of height between the vertebrae), and in the case of fusion devices, insufficient bony integration and joining of the implant with the adjacent endplates of the vertebral bodies (insufficient fusion).

In the context of fusion devices, most have mechanical properties that approximate the properties of cortical bone, but overall, the constructs are substantially stiffer than cancellous bone, and those made with polymers, such as PEEK, are not osteoconductive. It is believed that these features adversely affect the overall success of fusion implants and contribute to the modes of failure described above.

In the specific context of cervical and lumbar artificial disc replacements, articulating surfaces are used to restore motion, but these devices are typically not suited to deliver motion in all six degrees of freedom (which include yaw, pitch, roll, Left/Right lateral, up/down along the cranial to caudal axis, & forward/backward in the plane from anterior to posterior) because such devices include mechanical hinge-like features that have fewer degrees of freedom. Over the past twenty-five years, several attempts have been made to develop a viscoelastic disc using titanium endplates and a polymer core with a low durometer wherein the polymer could theoretically allow for movement in all of the degrees of freedom. Most of the failures with these devices have occurred because of the inability to consistently establish a bond between the endplates to the polymer core. The internal endplate surfaces are usually covered with titanium beads or one or more other porous structures, and the endplates may include multiple parts that must be joined together with the assembly with the polymer, and the polymer is either heated and compressed between the beads or injection molded. Sometimes chemicals have been added to etch and prime the titanium beads, but failures still occurred in-vivo or under shear loads due to failures within the multi part endplates and the insufficiently affixed polymer.

Thus, there is a need in the art for spinal implant constructs, both interbody fusion devices and artificial discs, with mechanical properties that more closely match the properties of cortical bone, and in the context of fusion devices, are osteoconductive, and have structural features that enhance the inter-engagement between the polymer and the endplates in a construct that is effectively unitary.

SUMMARY

In various embodiments, provided here are orthopedic implants useful for any of a variety of applications, including but not limited to spinal and extremity applications, such as knee and shoulder arthroplasty. In some particular embodiments, an implant is suitable for spinal applications for disc replacement, and for spinal fusion, in any one of the lumbar, thoracic and cervical spine.

The implants are constructs of one or two rigid monolithic plates, each plate formed as a unitary structure without any separately assembled parts. The implants also include a core that is integrally formed within an interior space within a plate. In some particular embodiments, the constructs include a single plate and a core wherein cooperating portions of the rigid monolithic plate and the core are interengaged, and where each of the core and the rigid monolithic plate have tissue-contacting faces. According to such embodiments, the constructs may be used for any of a variety of orthopedic applications, such as long bone joint arthroplasty, or articulating joints such as fingers and toes.

In other particular embodiments, the constructs include two plates between which is a core that is interengaged with each plate, the two plates thereby forming a generally disc shaped construct with opposing tissue contacting surfaces. According to such embodiments, the constructs are suitable, for example for spinal interbody fusion and artificial disc applications. In some specific embodiments, the core is formed of an elastomeric material. And in further specific embodiments, the construct includes one or more through holes that are generally center relative to an external periphery of the disc shaped construct. As more specifically described herein, such constructs may be used for one or more of spinal fusion and dynamic replacement of a disc without fusion, and may be delivered by any one of a variety of modes of access, including open and minimally invasive modes, and further including, lateral, anterior, posterior, transforaminal, extreme lateral, and others.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
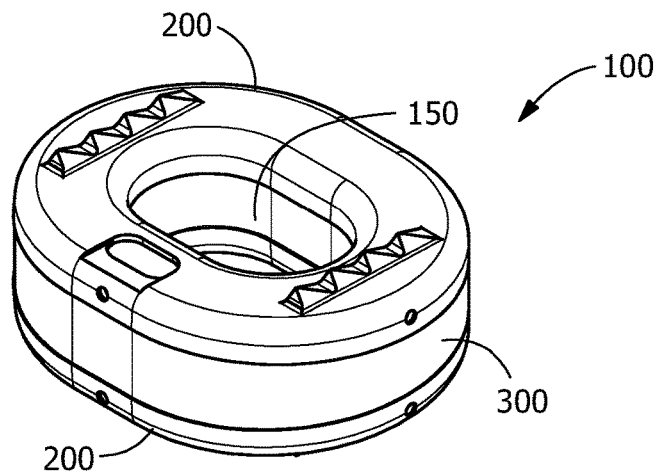
FIG. 1 shows an embodiment of an implant construct according to the disclosure.

Reference numerals as may be used herein are intended to facilitate illustration and are not intended to be limiting in any way and include:

| | |
|---|---|
| Implant construct 100 | interior face circumferential wall 270 |
| Rigid monolithic plates 200, 700, 800, 900, 1000, 1100, 1200 | interior plate wall 280 |
| core 300 | flow hole 290 |
| center through hole 150 | core body 310 |
| tissue contacting surface 210 | contact surfaces 320 |
| tissue engagement feature 220 | core exterior wall 330 |
| circumferential rim of plate 230 | center through hole wall 340 |
| center hole circumferential rim 235 | outflow fill 350 |
| core engagement surface 240 | undercut 550 |
| apertures 250 | apertures 650, 950, 1150, 1250 |
| hollow interior 260, 850 | struts 1270 |

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts may be embodied in different forms and should not be construed as limited to the embodiments set forth herein. Rather, these embodiments are provided so that this disclosure will be thorough and complete, and will fully convey the scope of the general inventive concepts to those skilled in the art.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community. One of ordinary skill will appreciate that references to positions in the body are merely representative for a particular surgical approach.

For example, the application may include reference to the following terms: "cephalad," "cranial" and "superior" indicate a direction toward the head, and the terms "caudad" "caudal" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient. The term "medial" indicates a direction toward the mid line of the patient, and away from the side, the term "ipsalateral" indicates a direction toward a side that is proximal to the operator or the object being referenced, and the term "contralateral" indicates a direction toward a side that is distal to the operator or the object being referenced. More generally, any and all terms providing spatial references to anatomical features shall have meaning that is customary in the art.

"Patient" is used to describe an animal, preferably a human, to whom treatment is administered, including prophylactic treatment with the compositions of the present invention. "Concave" is used herein to describe an indented surface without reference to the specific shape of the indented surface. As non-limiting examples, the concave face may be tubular with a round cross section, oval cross section, square cross section, or rectangular cross section.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits.

In various embodiments, provided here are orthopedic implants useful for any of a variety of applications, including but not limited to spinal applications, and extremity applications, such as knee and shoulder arthroplasty. In some particular embodiments, an implant is suitable for spinal applications for disc replacement, and for spinal fusion, in any one of the lumbar, thoracic and cervical spine. The implants are constructs of one or two rigid monolithic plates 200 and a core 300 that is integrally formed within an interior space within a plate. Referring now to FIG. 1, the implant constructs 100 may include two rigid monolithic plates 200 and a core 300. In some particular embodiments, the constructs include a single rigid monolithic plate 200 and a core 300 wherein cooperating portions of the rigid monolithic plate 200 and the core 300 are interengaged, and where each of the core 300 and the rigid monolithic plate 200 have tissue-contacting faces 320 and 210, respectively. In other particular embodiments, the constructs include two rigid monolithic plates 200 between which is a core 300 that is interengaged with each rigid monolithic plate 200, the two rigid monolithic plates 200 thereby forming a generally disc shaped construct with opposing tissue contacting surfaces 210.

According to such embodiments, the constructs are suitable, for example for spinal interbody fusion and artificial disc applications. In some specific embodiments, the core 300 is formed of an elastomeric material. And in further specific embodiments, the construct includes one or more through holes 150 that are generally center relative to an external periphery of the disc shaped construct. As more specifically described herein, such constructs may be used for one of more of spinal fusion and dynamic replacement of a disc without fusion, and may be delivered by any one of a variety of modes of access, including open and minimally invasive modes, and further including, lateral, anterior, posterior, transforaminal, extreme lateral, and others.

Conventional spinal implants suffer from a variety of modes of failure. Devices that are "too strong" with higher modulus of elasticity relative to adjacent bone (particularly cancellous), lead to bone failures characterized by subsidence, under-correction of lordosis/kyphosis, and effective loss of correction. Devices that are "too weak" with lower modulus of elasticity relative to adjacent bone can lead to device failure and effective loss of correction. In general, interbody fusion devices tend to be too strong. And in contrast, dynamic devices, such as for example, dynamic cervical discs designed like a joint, can exhibit hypermobility and instability. Cancellous bone has a modulus of 0.45 GPa, while the cortical rim has a modulus of 12.7 GPa. Interbody devices are positioned at the cortical rim and on the cancellous bone, where subsidence, loss of correction and fusion all occur. Conventional devices, such as interbody fusion deices, are made of any of a variety of materials selected from 3D Titanium (3.0 GPa, approximately 7 times stiffer than cancellous bone and osteoconductive), PEEK (3.5 GPa, approximately 8 times stiffer than cancellous bone and not osteoconductive), Titanium (120 GPa, approximately 100 times stiffer than cancellous bone and osteoconductive, and, PEEK with Titanium endplates (more osteoconductive than PEEK alone, but still approximately 8 times stiffer than cancellous bone).

Without being bound by theory or mechanism, the inventors hereof provide implants that may be varied in the combination of core material, core dimensions, and inclusion of none, one, or more center through holes, the dimensions of which may be varied, to enable each of two distinct benefits for overcoming the limitations in the art. Thus, for fusion applications, in one aspect, the implant constructs may be customized to most closely match the mechanical properties of adjacent bone, most particularly of cancellous bone, to overcome the subsidence problems associated with constructs made only of titanium and also provide the enhanced opportunity for fusion that are limited in polymer (e.g. PEEK) constructs. And in another aspect, for both fusion and disc replacement applications, the constructs comprising one or more center through holes provide for additional mechanical stress relief of the elastomeric core around the inner circumferential wall to thereby reduce the likelihood of shear and torsional failure and delamination of the core from the interior wall of the plate.

According to the disclosure, embodiments hereof may, thus, include two titanium, hollow endplates with internal cavities that are filled and with the viscoelastic core. To modify the mechanical characteristics, in one example a hole or pocket that is uniform or non-uniform in shape, such as, for example an oval, may be added to the construct. For simplicity, this feature will be referred to as the center hole. Using insert injection molding or compression molding, the internal cavities are filled with an elastomeric polymer to create a mechanical bond between the endplates and the core. This is accomplished by having floe hole(s) or entry points on the underside or rims of the endplates and site/exit holes along the side and/or top or rims of the endplates to ensure the cavity is completely filled with polymer by directing flow and ensuring air is pushed out to avoid pockets. In various embodiments, the interior walls of the monolithic plate are beveled, chamfered or radiused to enhance the available contact surface particularly around the circumferential rim 230 and enhance adhesion of the polymer. The center hole, if one is used, may go through both endplates and the core, or may be present only in the core, or only in the core and one endplate, or only in the endplates, and may vary in size and shape to change the modulus of elasticity (stiffness) of the device. The durometer of the polymer may also be changed to allow for adjustment of the overall stiffness of the implant to either improve fusion or motion, depending on whether the implant is being used for fusion or motion restoration. For interbody fusion implants, the center hole will be filled with bone graft material and the lower modulus of the invention will allow for more load to be transferred both axially and circumferentially. According to Wolff's Law, a lower modulus will transfer more load to the bone graft in a center core of a fusion device, leading to superior fusion rates, while reducing both subsidence and loss of correction. The improvements will lead to better clinical results. If the hole is not filled with bone graft or the device does not have a center hole, then the device will act like an artificial disc and loads will be distributed uniformly across the device. According to the various embodiments of implant constructs herein, increasing or decreasing the size and shape of the one or more center holes, together with other variables as described herein above, can reduce or increase the amount of polymer material used, to further accomplish modification of the construct's overall modulus of elasticity/stiffness. In various such embodiments, the implant construct characteristics can be matched to the physical characteristics of a patient (i.e. weight and bone density).

Implant Constructs

Figure 2:
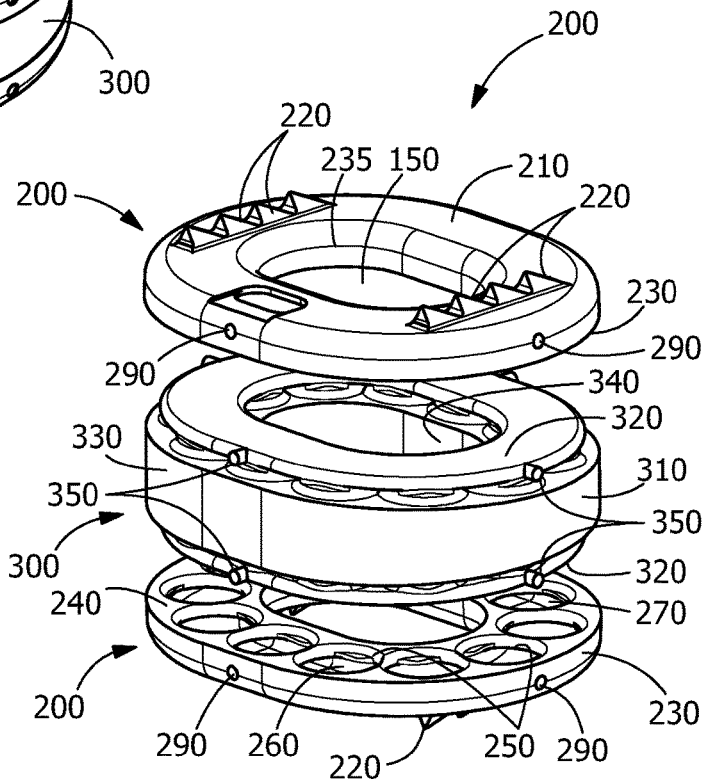
FIG. 2 shows the implant construct as shown in FIG. 1 wherein the components of the construct are shown in an exploded view.

Referring again to the drawings, FIG. 2 depicts a representative implant construct 100 comprising two rigid monolithic plates 200.

Rigid Monolithic Plates

In the various embodiments the implant constructs 100 include at least one rigid monolithic plate 200 that has a generally disc-like shape. Each rigid monolithic plate 200 includes two opposing walls joined by a circumferential rim 230 to define a hollow interior 260. Each of the walls and rim have interior (280 and 270) and exterior faces. One wall of the rigid monolithic plate 200 includes a tissue-contacting surface 210 on its exterior face. The other wall includes on its exterior face a core engagement surface 240 that includes one or a plurality of apertures 250 that open into the hollow interior 260 for integral engagement with the core 300. As shown in each of the drawings FIG. 4-11, a variety of different shaped monolithic plates are shown, having features selected from overall shape, through holes and through hole shapes, and aperture shapes, and combinations of these, that vary in accordance with the specific descriptions as described herein below.

The interior face 280 of each of the walls is substantially planar, and may be smooth or may include any of a variety of tissue engagement features 220 including features that encourage adhesion with the core 300. In the various embodiments, the circumferential rim 230 includes an inner surface 270 that is one or more of radiused, chamfered and beveled. In some embodiments, the interior rim face 270 of the circumferential rim 230 is continuously radiused from each of the interior faces of the rigid monolithic plate 200 walls. In some specific embodiments, the interior rim face 270 includes a bevel or chamfer. In other embodiments, the circumferential rim 230 interior rim face 270 includes radiused, beveled or chamfered corners at each of the interfaces with the interior plate walls 280, wherein the corners are connected by a circumferential rim wall that is one of planer and radiused. Likewise, the rigid monolithic plates 200 that comprise a center through hole 150 include an center hole circumferential rim 235 that also has an interior rim face 270, wherein that interior rim face 270 is one or more of radiused, chamfered and beveled, wherein in some embodiments it is continuously radiused from each of the interior faces 280 of the rigid monolithic plate 200 walls, and in some specific embodiments, the interior rim face 270 includes a bevel or chamfer. In some particular embodiments, the center hole circumferential rim 235 has an interior rim face 270 that includes radiused, beveled or chamfered corners at each of the interfaces with the interior plate walls 280, wherein the corners are connected by a circumferential rim wall that is one of planer and radiused.

In the various embodiments, the rigid monolithic plate 200 is formed of a material selected from the group consisting of metals and polymer composites. Thus, in the various embodiments, the rigid monolithic plate 200 material may be formed of any of a variety of materials that are selected from metals and polymers that are well known in the art. In a specific example, the rigid monolithic plate 200 is formed of a material comprising titanium.

In the various embodiments, the one or plurality of apertures 250 of the core engagement surface 240 of the rigid monolithic plate 200 has a shape selected from the group consisting of triangular, circular, oval, reniform (bean shaped), and combinations of these.

In some embodiments, as shown for example in FIG. 2, the rigid monolithic plate 200 comprises on its tissue-contacting surface 210 one or more features for engagement with tissue, such tissue engagement features 220 selected from the group consisting of ridges, knurls, channels, teeth, fins, hydroxyapatite, nanostructures, and microstructures.

In some specific embodiments, a rigid monolithic plate 200 may include one or a plurality of flow holes 290 positioned on an outer surface, such as, for example, on the circumferential rim 230. The flow holes 290 facilitate directional flow of the core 300 material introduced into the rigid monolithic plate 200 by a process such as injection molding to ensure complete or near complete filling of the plate's hollow interior 260. It will be appreciated that in other embodiments, the flow holes 290 may be more or fewer, and may be positioned on the rigid monolithic plate 200 at any of various positions to facilitate flow of flowable polymer.

Core

In the various embodiments the implant constructs 100 also include a core 300 having a generally disc-like shape that is complimentary to the shape of the at least one rigid monolithic plate 200. The core 300 includes a core body 310, a first side, a circumferential external wall, and a second side that is opposite the first side, each of the first and second sides having contact surfaces 320 for one of tissue and a core engagement surface 240 of a rigid monolithic plate 200. The first side is integrally engaged with and has contact surfaces 320 that include the interface surface 325 that is essentially coextensive with the interior surfaces of the walls 280 and circumferential rim surfaces (of the circumferential rim and any through hole circumferential rim) 270 of the hollow interior 260 of the rigid monolithic plate 200. The core 300 is continuous through the one or more apertures 250 in the core engagement surface 240 and substantially occupies the entire interior space of the plate. In some embodiments, the core 300 may further comprise one or more outflow fill 350 features that comprise polymer that filled an inflow or outflow hole 290 in a rigid monolithic plate 200 as an artifact of injection or other flow molding process, the outflow fill 350 providing supplemental adhesion benefit to the overall implant construct 100.

In accordance with the various embodiments, the core 300 may comprise any of a variety of materials, including but not limited to polymers. In some specific examples, the core 300 comprises an elastomer. And in even more specific examples, the core 300 comprises an elastomer selected from thermoplastic polyurethanes. Thermoplastic polyurethane can be obtained from, for example, Lubrizol Life Science Polymers (sold under the trademark Carbothan, similar to Bionate).

One Plate and Two Plate Constructs

In accordance with the various embodiments, the at least one rigid monolithic plate 200 and the core 300 are interengaged to provide an essentially unitary implant construct 100. In accordance with the various embodiments, the construct that includes the at least one rigid monolithic plate 200 and the core 300 has a disc like shape that is one of circular and oblong, where each of the at least one rigid monolithic plate 200 and the core 300 is circular or oblong. In some specific embodiments, the construct is generally elliptical, and has an outer periphery that includes the exposed circumferential rim 230 of the at least one rigid monolithic plate 200 and the core 300, wherein each of the rigid monolithic plate 200 and the core 300 may have height dimensions that are the same or different, and wherein each of the at least one rigid monolithic plate 200 and core 300 have overall width and length dimensions that are essentially equivalent.

In some specific embodiments, the construct comprising the mechanically interengaged at least one rigid monolithic plate 200 and core 300 includes one of a center through hole 150 and a plurality of generally centered through holes 150. Thus, in such embodiments, each of the at least one rigid monolithic plate 200 and core 300, individually, includes one of a center through hole 150 and a plurality of generally centered through holes 150. According to such embodiments, the one or more center through hole 150 has a shape selected from the group consisting of triangular, circular, oval, reniform, irregular and combinations of these. In such embodiments, the one or more center through holes 150 are generally arranged centrally relative to a center axis of the construct (and thus a shared center axis of each of the at least one rigid monolithic plate 200 and core 300). In some specific embodiments, the construct includes a single center through hole 150, and in some specific embodiments there may be more than one through hole. In some particular embodiments, there is a single center through hole 150 having a shape that is selected from circular and oval (oblong).

In accordance with the embodiments in which the implant construct 100 includes one or more center through holes 150, each such center through hole 150 defines an inner circumferential wall which includes an inner circumferential rim 235 of the at least one rigid monolithic plate 200 and an inner wall (center through hole wall) 340 of the core 300. It will be clear that the shape and contour of the inner circumferential rim 235 of the at least one rigid monolithic plate 200 and an inner wall (center through hole wall) 340 of the core 300 will be defined by the shape of the center through hole 150, which may be of any shape, including but not limited to triangular, circular, oval, reniform, and irregular. Each of the core 300 and rigid monolithic plates 200 has, respectively, at least one center through hole wall 340 and one center hole circumferential rim 235, or a greater number thereof in the instance of more than one through hole. In fusion embodiments, these inner circumferential rim 235 of the at least one rigid monolithic plate 200 and an inner wall (center through hole wall) 340 of the core 300 surfaces may be adapted to enhance osseointegration and may thus include surface texture, features or treatments.

In some specific embodiments, the construct includes two rigid monolithic plates 200 and a core 300. And in some such embodiments, the construct is a spinal implant useful for applications selected from disc replacement and fusion. Referring again to FIG. 1, the spinal implant construct 100 is a construct having a center through hole 150 and an elastomeric core 300 positioned between and engaged with two rigid monolithic plates 200. As shown, each rigid monolithic plate 200 has a generally disc-like shape with two opposing walls joined by a circumferential rim 230 to define a hollow interior 260. Also as shown, each of the walls and circumferential rim 230 has an interior face and an exterior face. Referring now to FIG. 2, specifically in reference to each of the two rigid monolithic plates 200, one wall has on its exterior face a tissue-contacting surface 210, and the other wall has on its exterior face a core engagement surface 240. According to the depicted embodiment as shown in FIG. 2, the core engagement surface 240 includes a plurality of apertures 250 that open into the hollow interior 260, the depicted apertures 250 being generally circular in shape, each aperture 250 having about the same overall dimensions, and radiused edges.

Figure 3:
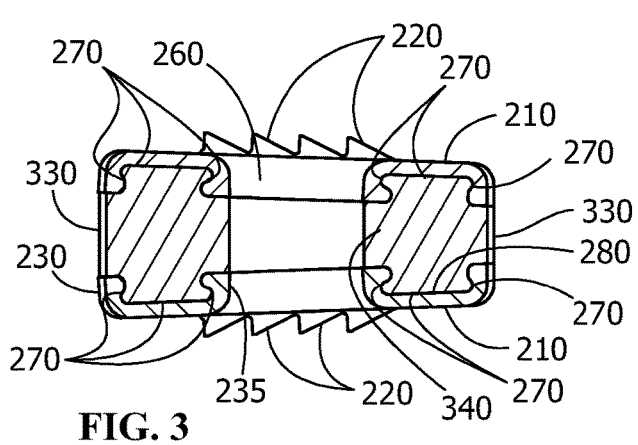
FIG. 3 shows the assembled implant construct of FIG. 1 in cross section.
Figure 4:
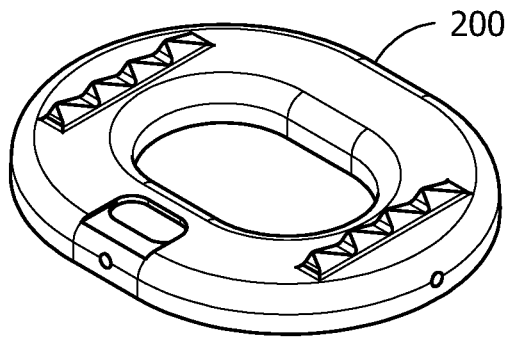
FIG. 4 shows an embodiment of a rigid monolithic plate of an implant construct as shown in FIG. 1, the rigid monolithic plate shown in top view (tissue contacting surface perspective) and having an overall oval or oblong shape.
Figure 5:
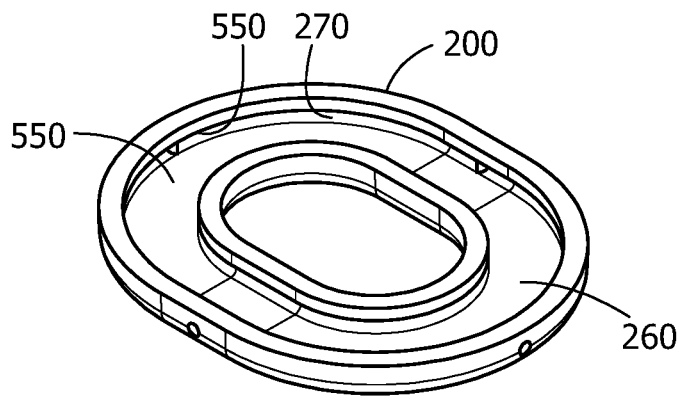
FIG. 5 shows an alternate embodiment of a rigid monolithic plate from a bottom view (core engagement surface) perspective, the rigid monolithic plate having a single undercut aperture.
Figure 6:
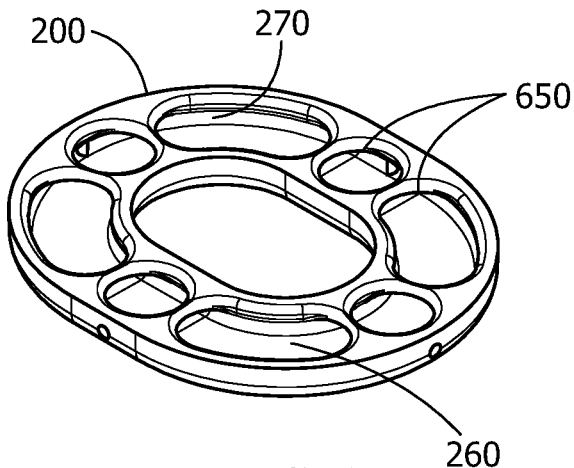
FIG. 6 shows an alternate embodiment of a rigid monolithic plate from a bottom view (core engagement surface) perspective, the rigid monolithic plate having an array of round and reniform apertures arranged concentric with the outer and inner circumferential walls of the construct.
Figure 7:
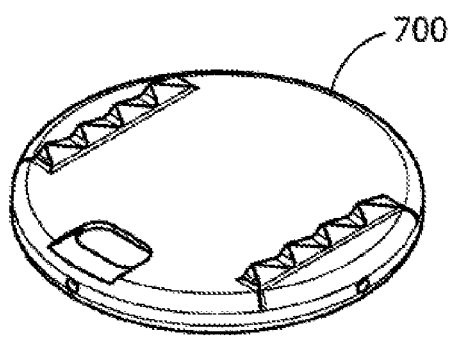
FIG. 7 shows an alternate embodiment of a rigid monolithic plate of an implant construct, the rigid monolithic plate shown in top view (tissue contacting surface perspective) and having an overall round shape without a center through hole.
Figure 8:
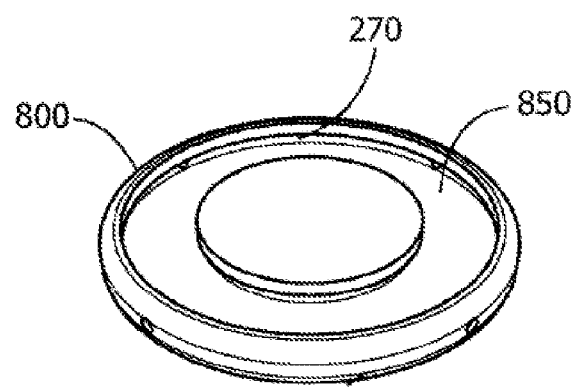
FIG. 8 shows an alternate embodiment of a rigid monolithic plate from a bottom view (core engagement surface) perspective, the rigid monolithic plate being round and having a single undercut aperture (core engagement surface) with a through hole.
Figure 9:
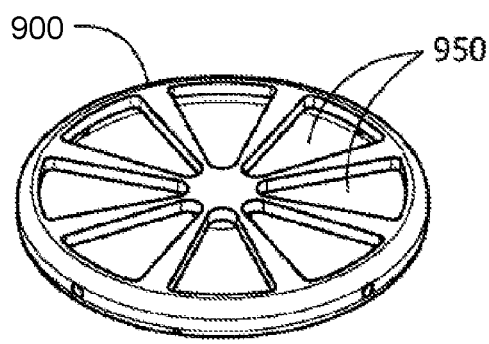
FIG. 9 shows an alternate embodiment of a rigid monolithic plate from a bottom view (core engagement surface) perspective, the rigid monolithic plate being round and having a plurality of triangular wedge shaped apertures (core engagement surface) arranged symmetrically around a center axis without a through hole.
Figure 10:
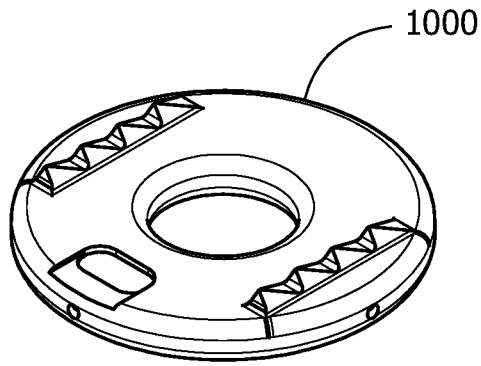
FIG. 10 shows an alternate embodiment of a rigid monolithic plate of an implant construct, the rigid monolithic plate shown in top view (tissue contacting surface perspective) and having an overall round shape with a center through hole.
Figure 11:
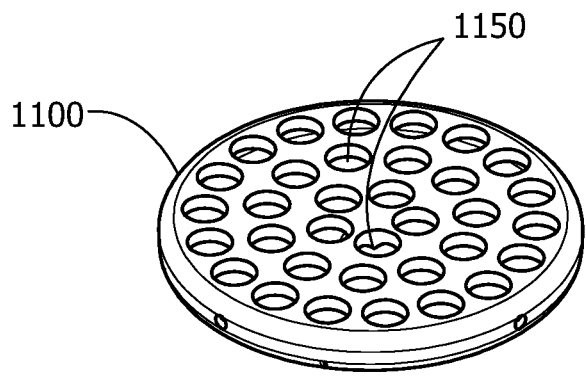
FIG. 11 shows an alternate embodiment of a rigid monolithic plate from a bottom view (core engagement surface) perspective, the rigid monolithic plate being round and having a plurality of round shaped apertures (core engagement surface) arranged symmetrically around a center axis without a through hole; and, FIG. 12 shows an alternate embodiment of a construct without a core according to the disclosure, the construct having a generally circular shape with a round center through hole, each of the rigid monolithic plates including a plurality of round shaped apertures on their core engagement surfaces, the apertures arranged symmetrically around a center axis, and the construct including an array of struts spaced around the periphery between each of the opposing plates.

It will be appreciated by one of ordinary skill that in alternate embodiments, the apertures 250 may be of varied shape and may have the same or different dimensions, and they may be arrayed in an ordered or random fashion on the face of the plate. Also as shown in the depicted embodiment, each rigid monolithic plate 200 includes on its circumferential rim 230 and at least one flow hole 290. It will further be appreciated that a rigid monolithic plate 200 may include more or fewer flow holes 290, and the flow holes 290 may be of any of a variety of shapes including shapes selected from the group consisting of triangular, circular, oval, reniform, irregular and combinations of these. Again with reference to FIG. 2, and also with reference to FIG. 3, the interior face of each of the walls is substantially planar and the interior face of the circumferential rim 230 is radiused. As shown, the core 300 also has a generally disc-like shape that is complimentary to the shape of the rigid monolithic plates 200 and includes a center through hole 150 that is oval. As shown in FIG. 1 and FIG. 3, each of the first side and second side of the elastomeric core 300 is integrally engaged with and has an interface surface 325 that is essentially coextensive with the interior surface of the wall and circumferential rim 230 of the hollow interior 260 of a rigid monolithic plate 200.

Referring again to FIG. 3, the depicted construct is wedged shape, with an overall height dimension that varies from one side to the other along the width dimension (i.e., along the plane that transects the construct from front to back and corresponding to the AP plane as the implant construct 100 would be oriented between adjacent vertebrae. It will be appreciated that, in general, a spinal construct as shown in each of FIG. 1-FIG. 3 may have a height dimension that is fixed or one that varies along one or both of the long (typically the lateral) and short axis (anterior to posterior) of the implant construct 100. And in some embodiments, the construct 100 may be generally lordotic or kyphotic (i.e., having a height that varies from front to back (anterior to posterior) relative to the generally curvature of the spinal level at which the construct 100 will be implanted.

In accordance with the depicted embodiment, the construct 100 is suitable in particular for implantation to achieve either dynamic disc replacement or fusion. Thus, in some embodiments wherein the implant construct 100 is intended for disc replacement, the overall stiffness of the implant construct 100 may be varied to allow for dynamic motion by varying one or more of elastomer durometer, one or more size dimensions of the elastomeric core 300, and one or more of shape, dimension and number of center through holes 150. According to such embodiments, the construct having a center through hole 150 would allow for achieving dynamic motion while also minimizing the amount of internal stress on the core 300. In some other embodiments, the implant construct 100 may not include a center through hole 150.

Referring again to FIG. 1, in an alternate application for spinal implantation, the implant construct 100 is advantageously used with one or more bone inducing materials that may be inserted in the one or more center through holes 150 to encourage bony ingrowth therein for achieving fusion with and between the adjacent vertebrae.

Figure 12:
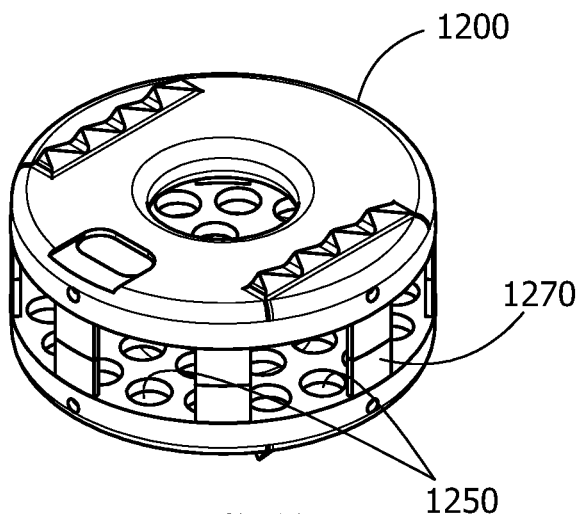

Referring now to FIG. 12, yet another embodiment of implant is shown, the overall disc like shape being generally circular. The implant construct 100 is shown without a core 300 for clear illustration of the features of the rigid monolithic plates 200. As shown, this alternate embodiment includes peripheral struts 1270 that can provide enhanced strength and confer greater stiffness to the device, suitable for example for fusion applications.

Examples

In one embodiment, an implant construct 100 includes: 1. Titanium endplates with a cavity and hole(s)/entry points on the surfaces facing the core, and a 2. Polymer core with or without a center hole(s) through the center. The endplates are manufactured using DMLS and/or other additive manufacturing processes to create a monolithic construct having an interior cavity and apertures 250 for the elastomeric core 300. The endplates are placed in a mold and the uncured elastomeric polymer is injected into the mold to bond the endplates with the core 300 by filling the cavities to create a mechanical bond. Radiused edges of the apertures 250 and the radiused inner wall of the circumferential rim 230 enhance adhesion of the polymer with the endplates.

The outer surface of the construct 100 may be designed for bony ingrowth and its inner surface, cavity, and hole(s) for bonding the endplates and core 300. A center through hole 150 will confer greater construct compressibility under pressure to transfer loads to the bone graft material inside the center hole 150 or to restore motion in the absence of fusion.

After removing most of the spinal disc, a surgeon will implant the construct 100 between two vertebral bodies where disc used to be located in the patient.

In one representative example, a construct 100 for fusion applications includes a construct with a High Durometer TPU core w/DMLS endplates for Heavy Patients (for example, for a patient who is a 250 lb former pro football player). The construct 100, will have reduced stiffness as compared with titanium constructs, greater stiffness than PEEK constructs with the benefit of enhanced osseointegrative features conferred by the titanium endplates and through hole and enhanced resistance to device failure by virtue of the design that includes a through hole and inter-engaged monolithic endplates 200 and elastomeric core 100.

In another representative example, a construct for fusion applications includes a construct with a Low Durometer TPU w/DMLS endplates for Light Patients (for example, for a patient who is an 85 lb. former gymnast).

In yet another representative example, a construct for dynamic disc replacement applications includes a construct with a Lowest Durometer TPU with DMLS endplates for motion restoration/preservation.

While the disclosed embodiments have been described and depicted in the drawings in the context of the human spine, it should be understood by one of ordinary skill that all or various aspects of the embodiments hereof may be used in connection with other species and within any species on other parts of the body where deep access within the tissue is desirable.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

What is claimed is:

1. An orthopedic implant, comprising:
   (i) a rigid monolithic plate having a generally disc-like shape and comprising first and second opposing walls joined by a circumferential rim that define a hollow interior, each of the walls and rim having an interior and exterior face, the first wall comprising on its exterior face a tissue-contacting surface, the second wall comprising on its exterior face a core engagement surface and one or a plurality of apertures that open into the hollow interior,
   (ii) a core having a generally disc-like shape that is complimentary to the shape of the rigid monolithic plate, and comprising a core body, a first side, a circumferential external wall, and a second side that is opposite the first side, wherein the first side extends through the one or plurality of apertures and into the hollow interior where the first side of the core is integrally engaged with and has an interface surface that is coextensive with at least one of the interior faces of the first and second walls and the rim of the rigid monolithic plate;
   wherein the rigid monolithic plate and the core are engaged to provide a unitary construct.

2. An orthopedic implant according to claim 1, further comprising:
   a second rigid monolithic plate having a generally disc-like shape and comprising two opposing walls joined by a circumferential rim that define a hollow interior, each of the walls and rim having an interior and exterior face, one wall comprising on its exterior face a tissue-contacting surface, the other wall comprising on its exterior face a core engagement surface and one or a plurality of apertures that open into the hollow interior, and the interior face of each of the walls is substantially planar and the interior face of the circumferential rim is one or more of radiused, chamfered and beveled,
   wherein the second side of the core is integrally engaged with and has an interface surface that is coextensive with the interior surface of the hollow interior of the second rigid monolithic plate, and
   wherein the rigid monolithic plate, the core and the second rigid monolithic plate are mechanically engaged to provide a unitary construct.

3. An orthopedic implant according to claim 2 wherein the construct comprising the mechanically engaged rigid monolithic plate, elastomeric core, and second rigid monolithic plate includes a center through hole, the center through hole having a shape selected from the group consisting of triangular, circular, oval, reniform, irregular and combinations of these.

4. An orthopedic implant according to claim 1 wherein the core comprises an elastomer.

5. An orthopedic implant according to claim 4 wherein the elastomer is selected from thermoplastic polyurethanes.

6. An orthopedic implant according to claim 1 wherein the rigid monolithic plate is formed of a material selected from the group consisting of metals and polymer composites.

7. An orthopedic implant according to claim 6 wherein the rigid monolithic plate is formed of a material comprising titanium.

8. An orthopedic implant according to claim 1 wherein the one or plurality of apertures of the second wall of the rigid monolithic plate has a shape selected from the group consisting of triangular, circular, oval, reniform, and combinations of these.

9. An orthopedic implant according to claim 1 wherein the disc-like shape of the rigid monolithic plate and core is selected from circular and oblong.

10. An orthopedic implant according to claim 9 wherein the rigid monolithic plate and core are oblong.

11. An orthopedic implant according to claim 1 wherein the rigid monolithic plate comprises on its tissue-contacting surface one or more features for engagement with tissue selected from the group consisting of ridges, knurls, channels, teeth, fins, hydroxyapatite, nanostructures, and microstructures.

12. The orthopedic implant according to claim 1 wherein the hollow interior extends about an axis of the monolithic plate.

13. A spinal implant, comprising:
a construct comprising an elastomeric core positioned between and engaged with two rigid monolithic plates, the construct comprising:
(i) a pair of rigid monolithic plates, each rigid monolithic plate having a generally disc-like shape, and comprising two opposing walls joined by a circumferential rim, and a hollow interior,
wherein each of the walls and circumferential rim comprise an interior face and an exterior face, one wall comprising on its exterior face a tissue-contacting surface, the other wall comprising on its exterior face a core engagement surface and a plurality of apertures that open into the hollow interior, and each plate has a center through hole defining a plate inner rim and having a shape selected from the group consisting of triangular, circular, oval, reniform, irregular and combinations of these, and
wherein the interior face of each of the walls is substantially planar and the interior face of the circumferential rim is one or more of radiused, chamfered and beveled
(ii) an elastomeric core having a generally disc-like shape that is complimentary to the shape of the rigid monolithic plates, and comprising a core body, a first side, a circumferential external wall, a second side that is opposite the first side, and a center through hole, the core having a center through hole wall defining the center through hole thereof,
wherein the center through holes of the rigid monolithic plates and core each have a shape selected from the group consisting of triangular, circular, oval, reniform, irregular and combinations of these,
wherein each of the first side and second side of the elastomeric core are respectively disposed at least partially within the respective hollow interiors of the pair of rigid monolithic plates such that the first and second sides of the elastomeric core extend continuously within the hollow interiors about an axis defined by the center through holes of the monolithic plates and core.

14. A spinal implant according to claim 13 wherein the core comprises an elastomer selected from thermoplastic polyurethanes.

15. A spinal implant according to claim 13 wherein the rigid monolithic plates are formed of a material comprising titanium.

16. A spinal implant according to claim 13 wherein the one or plurality of apertures of the core engagement surface of each rigid monolithic plate has a shape selected from the group consisting of triangular, circular, oval, reniform, and combinations of these.

17. A spinal implant according to claim 13 wherein the disc-like shape of each rigid monolithic plate and the core is oblong.

18. A spinal implant according to claim 13 wherein the center through hole of the rigid monolithic plates and core are each oblong.

19. A spinal implant according to claim 13 wherein each of the rigid monolithic plates comprises on its tissue-contacting surface one or more features for engagement with tissue selected from the group consisting of ridges, knurls, channels, teeth, fins, hydroxyapatite, nanostructures, and microstructures.

20. A spinal implant according to claim 13 wherein each of the plates and the core comprise an oblong center through hole, and wherein the monolithic plates are formed of a material comprising titanium and the core is formed of an elastomeric material comprising a thermoplastic polyurethane, and wherein the core engagement surface of each rigid monolithic plate comprises a plurality of apertures that have a shape selected from reniform, round and a combination of these.

* * * * *